United States Patent [19]

Langberg et al.

[11] Patent Number: 4,985,925
[45] Date of Patent: Jan. 15, 1991

[54] ACTIVE NOISE REDUCTION SYSTEM

[75] Inventors: Edwin Langberg, Medford; F. Gerald Caruso, Palmyra, both of N.J.

[73] Assignee: Sensor Electronics, Inc., Mt. Laurel, N.J.

[21] Appl. No.: 210,791

[22] Filed: Jun. 24, 1988

[51] Int. Cl.$^5$ .............................................. A61F 11/02
[52] U.S. Cl. ......................................... 381/72; 381/71
[58] Field of Search ..................... 381/96, 71, 93, 83, 381/72

[56] References Cited

U.S. PATENT DOCUMENTS

| | | | |
|---|---|---|---|
| 4,395,588 | 7/1983 | Franssen et al. | 381/96 |
| 4,455,675 | 6/1984 | Bose et al. | 381/96 |
| 4,622,440 | 11/1986 | Slavin | 381/68 |
| 4,677,677 | 6/1987 | Eriksson | 381/71 |
| 4,783,818 | 11/1988 | Graupe et al. | 381/93 |
| 4,815,140 | 3/1989 | Wagner | 381/83 |
| 4,833,719 | 5/1989 | Carme et al. | 381/94 |

OTHER PUBLICATIONS

MF10 Universal Monolithic Dual Switched Capacitor Filter, National Semiconductor Data Sheet, (pp. 9–212 to 9–222), circa 1984.

*Primary Examiner*—Forester W. Isen

[57] ABSTRACT

Improvement in active noise reduction based on a negative feedback electro-acoustical system which consists of an Electronic Earplug seated in the concha fossa combining active and passive noise reduction in the quiet zone at the ear, a bilateral transducer circuit which drives a speaker as an acoustical velocity source, a shunt feedback control filter network which improves stability and increases noise reduction, and a combined input noise-filter/feedback system. A typical application is in a noisy environment for hearing protection and for improved communication capability, e.g., in vehicular communication, telephone, intercom, hearing aids, and stethoscopes.

18 Claims, 4 Drawing Sheets

ACTIVE NOISE REDUCTION SYSTEM

This invention was made with Government support under Contract DAMD17-85-C-5035 awarded by U.S. Army Medical Research Acquisition Activity. The Government has certain rights in this invention.

BACKGROUND

This invention relates in general to an improved method and apparatus for Active Noise Reduction (ANR) and more particularly to an ANR system at the ear with communication capability. The invention is a novel Electronic Earplug which combines active and passive noise reduction, a bilateral transducer drive, and a shunt feedback control correction network.

The Electronic Earplug is more compact, lighter, and less restrictive and requires less power to operate than headphone-based ANR systems which represent the closest known prior art.

A novel compensation of the electro-acoustic ANR feedback loop, based on the bilateral transducer drive and/or the shunt feedback control correction network maintains a satisfactory stability margin while generating a local sound counter wave. This counter wave is an acoustical means of active reduction of ambient noise which penetrates a passive plug barrier.

Active noise reduction is a negative feedback system, a concept which dates back to the seminal U.S. Pat. No. 1,686,792 by H. S. Black, issued in 1928. The specific application of negative feedback to an electro-acoustical ANR system was proposed in U.S. Pat. No. 2,983,790 by H. F. Olson, issued in 1961 and is described in articles by Olson and May (1953), and Olson (1956) and by Bleazey (1962). Such an ANR concept is summarized in FIG. 1 and is described in detail later. The ANR system in FIG. 1 produces an acoustical counter wave emanating from a speaker 15 which, under ideal circumstances, nearly cancels the effects of ambient noise $p_n$ which penetrates to a summing microphone 18. Hence, the microphone location defines a zone of acoustical quiet.

The ideal circumstances, mentioned above, imply that there is no phase shift around the feedback loop. In general, in an electro-acoustical system, phase shift is not constant but increases with frequency. It is therefore not possible to keep a constant phase shift over any extended frequency band. At a frequency where a 90° phase shift is reached, the ANR system in FIG. 1 no longer cancels noise. At a frequency where a phase shift of 180° is reached, negative feedback changes to positive feedback, and with sufficient gain, the system becomes unstable. The source of this undesirable frequency-dependent phase shift is twofold: sound wave propagation delay and acoustical circuit transmission delay.

Sound wave propagation delay is caused by the finite speed of sound in air which is approximately 344 m/sec. The phase shift caused by acoustical wave propagation delay is proportional to the distance over which the propagation delay is measured and to frequency, and is inversely proportional to the speed of sound. In an ANR system where distance between speaker and summing microphone 18 is short, phase shift caused by propagation delay is small. This makes the application of ANR in the Electronic Earplug very attractive. For example, for a speaker-microphone distance of 1 cm, a 180° propagation delay induced phase shift occurs at 17.2 kHz. For stability, the loop gain at 17.2 Hz frequency can be reduced well below unity without an adverse effect on speech communication which requires typically only a 200 Hz—4 kHz bandwidth.

With a speaker-microphone distance in the earplug of 1 cm or less, the overriding cause of instability is the phase shift caused by the acoustical circuit transmission delay. For example, as will be elaborated further in connection with FIG. 3, an acoustical circuit of a typical loudspeaker consists of a mass of the diaphragm, a compliance due to diaphragm and air support and a resistive component due to losses and acoustical radiation. The combined effect of the above acoustical circuit components is the diaphragm resonance which causes a 180° acoustical phase shift, often in the midst of the frequency region critically important to communication. Without the methods of compensation described later, diaphragm resonance and other acoustical circuit effects seriously limit the effectiveness of ANR systems.

Prior art closest to the Electronic Earplug is the use of ANR in headsets or headphones; e.g., as described in a paper by Dorey, A. P., Pelc, S. F., and Watson, P. R.: "An active noise reduction system for use with ear defenders". 8th International Aerospace Symposium, Cranfield, Mar. 24-27, 1975 and also more currently in U.S. Pat. Nos. 4,455,675 (Bose & Carter), 4,494,074 (Bose), and 4,644,581 (Sapiejewski).

Figure 1:
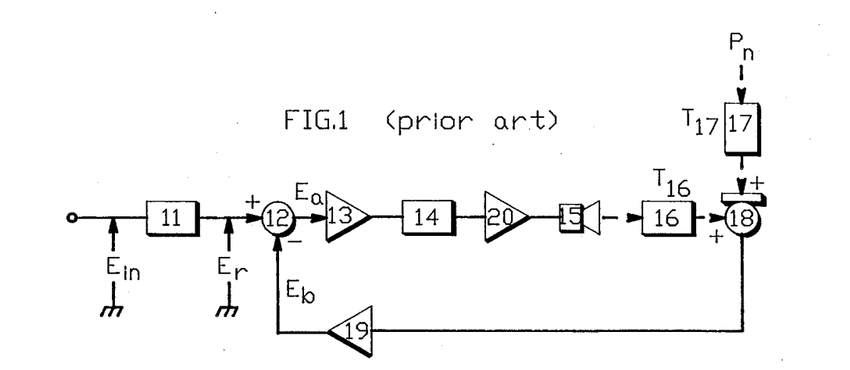
FIG. 1 is a block diagram of an electro-acoustical negative feedback loop in an Active Noise Reduction (ANR) system (prior art).

Prior ANR art, as represented in the references mentioned above, uses only cascade loop compensation, i.e., compensation circuits, such as represented by block 14 in FIG. 1, which are connected in series with other loop components. Present invention teaches an improvement of electro-acoustical feedback loop stabilization in the form of a speaker bridge circuit and shunt feedback control network, so that large loop gain can be used over a wide frequency range to provide high noise reduction while at the same time maintaining a satisfactory margin of stability.

Prior art of speaker compensation based on a bridge circuit is represented by U.S. Pat. No. 3,647,969 (Korn). A serious disadvantage of the bridge prior art is that it provides no means of automatically maintaining balance.

Prior art of amplifier compensation using shunt feedback control impedance across load for improvement of high frequency performance is reported by A. F. Arbel, *Analog Signal Processing and Instrumentation*, Cambridge University Press, pp. 133-138, 1980 and is reviewed by R. K. Jurgen in *IEEE Spectrum*. pp. 41-43, April, 1972.

SUMMARY OF THE INVENTION

The present invention is an improved Active Noise Reduction (ANR) and communication system. One object of the invention is an at-the-ear ANR system which is miniaturized to form an Electronic Earplug which maintains an acoustical seal with a concha fossa (the hollow which is external to the opening of the ear canal) and/or the external auditory meatus (ear canal).

Large passive noise attenuation is accomplished by providing a close-fitting acoustical barrier in the form of a resilient earplug adapter between the enclosure of the Electronic Earplug and its anatomical support in the vicinity of the orifice of the external auditory meatus. Noise which penetrates this passive barrier and reaches the quiet zone formed around the occluded ear canal volume adjacent to the eardrum, is further reduced by active means. Because this occluded volume of the quiet zone is small and well isolated, significantly larger noise reduction can be obtained in the Electronic Earplug system than in headphones with ANR. Also, the amount of power required to operate an Electronic Earplug is significantly less.

The small size and minimal protrusion of the Electronic Earplug are convenient. In some applications, i.e., when used with closely-fitting helmets or gas masks, the Electronic Earplug is indispensable since headphones cannot be accommodated. Electronic Earplugs are also safer than headphones in case of a side impact.

Another object of the invention is a bilateral transducer bridge circuit for simultaneously and directly sensing and correcting the mechanical motion of the diaphragm of a bilateral transducer. Compensation based on direct sensing of the diaphragm motion is very effective in eliminating adverse effects of diaphragm resonance. This bridge includes adaptive balancing means to maintain bridge balance in spite of variations in temperature and other variables which would otherwise imbalance the bridge.

Another objective of the invention is a feedforward circuit which significantly improves the stability and noise reduction properties of any ANR system.

For industrial and military hearing protection and communication, an Electronic Earplug has the following advantages:
  high ambient outside noise attenuation, even in the 20 Hz−1 kHz range,
  high fidelity communication channel,
  self monitoring of the effectiveness of hearing protection,
  modifiable response to accommodate hearing impairment,
  comfort, and small size and weight.

The Electronic Earplug adds communication and active noise reduction capability to the earplug. The Electronic Earplug can provide a 30 dB improvement in the 20 Hz−1 kHz range over and above the passive attenuation. Passive attenuation in this frequency range is hard to achieve with ordinary hearing protection, yet industrial machinery and vehicular operation typically generates most of its noise emission in this range. This is a very significant benefit of the Electronic Earplug for industrial and military hearing protection application.

The actual use of hearing protection depends to a large extent on positive acceptance by the user which is related to the comfort and non-interference of the hearing protection device. Electronic Earplugs are smaller, lighter, cooler, and more comfortable than earmuffs or earphones and they do not interfere with glasses, hardhats, or helmets. They therefore are very acceptable to the wearer.

The problem encountered with use of passive earplugs is that the temporomandibular joint motion may cause the earplug to imperceptibly back out of the ear canal and loose some of its hearing protection effectiveness. With Electronic Earplugs, the summing microphone can be used to monitor the sound pressure level (SPL) at the eardrum. If the SPL increases above a specified level, the Electronic Earplug can generate a warning light or sound which prompts the user to re-insert the earplug. This feature adds a new dimension in safety and verification of earplug operation.

With the Electronic Earplug, the occluded volume next to the eardrum is small and well isolated. As a result, greater active and passive noise reduction can be obtained than in headphones with ANR. Also, the amount of power required to operate the Electronic Earplug is significantly less than the power for headphones which is significant for battery operation.

For hearing aid application, the Electronic Earplug has the following advantages:
  improved direct ambient noise penetration without producing the feeling of "stuffiness" typical of unvented hearing aids,
  reduced outside noise penetration,
  reduced amplification distortion, and
  widening and smoothing of the hearing aid bandpass.

In the design of a hearing aid, the size of venting is a delicate compromise. Hearing aids are vented to produce a more natural, low-frequency response and to reduce the feeling of a stuffed ear which is a frequent complaint of the hearing aid users. Generous venting removes this feeling of fullness caused by occlusion but it opens up a path of ambient noise penetration. It also generates a potential for oscillation, caused by positive feedback, when part of the earphone sound reaches the external microphone via the vent.

ANR feedback changes the acoustical impedance of the occlusion at the eardrum and so removes the feeling of the stuffed ear and fullness which is a frequent complaint of hearing aid users. This is so, in spite of the fact that the earplug fits tightly in the ear canal, producing complete occlusion.

Another definite benefit of ANR with communication, typical of negative feedback, is the reduction of distortion in the microphone-earphone chain, as well as wider and smoother bandwidth.

In ordinary hearing aids, ambient acoustical noise penetrates to the eardrum with little attenuation. The Electronic Earplug-based hearing aid differs fundamentally in its ability to compensate for direct penetration of acoustical noise into the ear canal. Any component of the summing microphone signal which differs from the desired signal is attenuated by negative feedback. Consequently the Electronic Earplug reduces the ambient noise component as well as any other distortion in the hearing aid transmission. Closely related to the above application is the use of the Electronic Earplug is stethoscopes and Assistive Listening Devices (ALDS).

Hearing protection for firing ranges and artillery crews requires high impulse noise protection during the firing and minimal interference with normal listening between firings. Hearing protection based on ANR techniques described here lends itself to the above purpose.

A bilateral transducer bridge circuit provides the ability to control the phase and magnitude of acoustical radiation and reflection of the transducer diaphragm. Usefulness of this feature of the bilateral transducer bridge extends beyond the Electronic Earplug application. Shunt compensation technique of this invention also has broader application in feedback systems.

These and other objects of the invention will become apparent to those skilled in the art on consideration of the accompanying specification, claims, and drawings.

DETAILED DESCRIPTION OF THE PREFERRED EMBODIMENT

FIG. 1 depicts a typical prior art ANR negative feedback loop block diagram. FIG. 1 was mentioned earlier in the Background section in the discussion of the prior art.

An electro-acoustical negative feedback loop consists of a signal combiner 12 which subtracts a primary feedback signal $E_b$, which enters at the negative sign located at the bottom of signal combiner 12, from a reference input signal $E_r$, which enters at the plus sign located on the left of signal combiner 12. A difference signal, called an actuating signal, is applied to amplifier 13, is processed by a loop compensation circuit 14, and is applied to driver 20 which drives speaker 15.

Summing microphone 18 acts as a summing point for a signal emitted by speaker 15 and for local acoustical noise. Acoustical transfer function $T_{16}$ represents the acoustical transmission path 16 between speaker 15 and summing microphone 18. Noise transfer function $T_{17}$ represents the passive attenuation path 17 for ambient noise $p_n$ to the level of local noise in the quiet zone at summing microphone 18. Local noise level at summing microphone 18 is $p_{no}$ without ANR and $p_n$ with ANR. The summing microphone output signal amplified by preamplifier 19 produces the feedback signal $E_b$, thereby closing the loop.

The transfer function between output of amplifier 13 and output of speaker 15 describes the electro-acoustical path. The dotted lines between speaker 15, ambient noise source $p_n$ and terminating at the microphone 18 define an acoustical network. Summing microphone 18 and preamplifier 19 define an acousto-electrical path. The transfer function between the output of amplifier 13 and output of preamplifier 19 is defined as electro-acoustical transfer function $T_a$. An open loop transfer function is defined as the ratio $E_b/E_r$, with $E_b$ disconnected from signal combiner 12.

Electrical signal $E_{in}$, supplied by a communication channel, is pre-emphasized by filter 11 to compensate for any spectral distortion created by the ANR loop.

Figure 2:
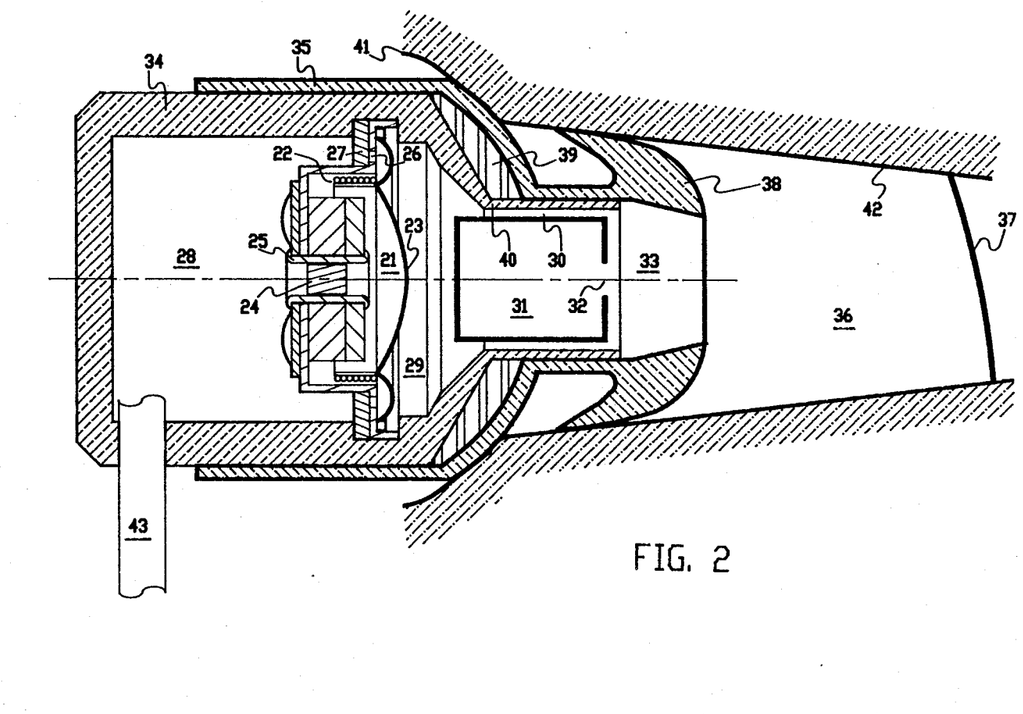
FIG. 2 is a cross-section view of an Electronic Earplug with a earplug adapter seated in the concha fossa with additional seal in the ear canal.

FIG. 2 shows a cross-section view of an Electronic Earplug which is seated in proximity to an opening of an ear canal. The Electronic Earplug combines passive and active noise reduction with optional communication capability. The Electronic Earplug provides passive attenuation by substantially closing the ear canal to direct noise penetration. Remaining noise which penetrates the passive attenuation and reaches the occluded ear canal in the vicinity of an eardrum is further reduced using electronic Active Noise Reduction means.

Components of the Electronic Earplug are mounted on enclosure 34. Electrodynamic transducer 21 serves as a speaker which provides a source of a local acoustical signal when coil 22, mechanically coupled to diaphragm 23, is energized. Typical of electrodynamic transducers, coil 22 moves in a magnetic field created in an air gap by a permanent magnet. The air on the inside of diaphragm 23 is coupled to a reference chamber 28 via acoustical resistor 24 in a hole of rivet 25 and through peripheral holes 26 backed up by a felt washer 27.

Transducer 21 not only drives the diaphragm 23 but also simultaneously senses velocity of diaphragm 23 using a circuit described later in conjunction with FIG. 4. The anti-reciprocal operation of the electrodynamic transducer; i.e., operation as a diaphragm actuator (speaker) and diaphragm velocity sensor (microphone) is well known. In fact, similar dual performance can be obtained from other types of reciprocal and anti-reciprocal acoustical transducers. In customary acoustical applications, reciprocal and anti-reciprocal transducers are used in a particular application either as a speaker or as a microphone. Here, transducer 21 when used simultaneously in a dual role i.e., as a speaker and as a microphone is referred to as a bilateral transducer.

Bilateral transducer 21 is located between the acoustical reference chamber 28 and a forward chamber 29. Forward chamber 29 is connected to a coaxial sound passage 30 between a summing microphone 31 and a nose 40 of the enclosure 34. Summing microphone 31 is a pressure-type electret microphone. Since the design of such microphones is well known, the internal details are omitted.

Earplug adapter 35, made of a silicon rubber elastomer, forms a skirt around enclosure 34, covers a compressed plastic foam washer 39, and then expands into a mushroom-shaped flange 38. An axial opening 33 in flange 38 connects the coaxial sound passage 30 and an orifice 32 in microphone 31 to an ear canal 36.

The plastic foam washer 39 is placed between the conical portion of enclosure 34 and the pliable silicone rubber skin of earplug adapter 35. This padded area of the earplug adapter is in contact with a concha fossa 41. The foam rubber padding assures both comfort and good fit. The silicone rubber provides a good acoustical seal at low acoustical frequencies which cannot be achieved by foam alone. Flange 38 provides another acoustical seal to wall 42 of the ear canal 36. As a result, the earplug adapter provides a dual acoustical seal (against concha fossa 41 and against the wall 42 of ear canal 36) so as to isolate eardrum 37 from unobstructed penetration of outside noise, without unduly constricting the acoustical coupling between summing microphone orifice 32 and the ear canal 36. To fit anatomical distribution of sizes, earplug adapters are available in several sizes.

A variety of other earplug adapters can be used with the Electronic Earplug. For example, a mushroom-shaped eartip adapter, commonly used with airline entertainment sets, can provide a seal largely external to the ear canal. On the other hand, a variety of hollow, single and multiple-flanged earplugs can provide a seal located inside the ear canal.

Figures 3, 4, 5:
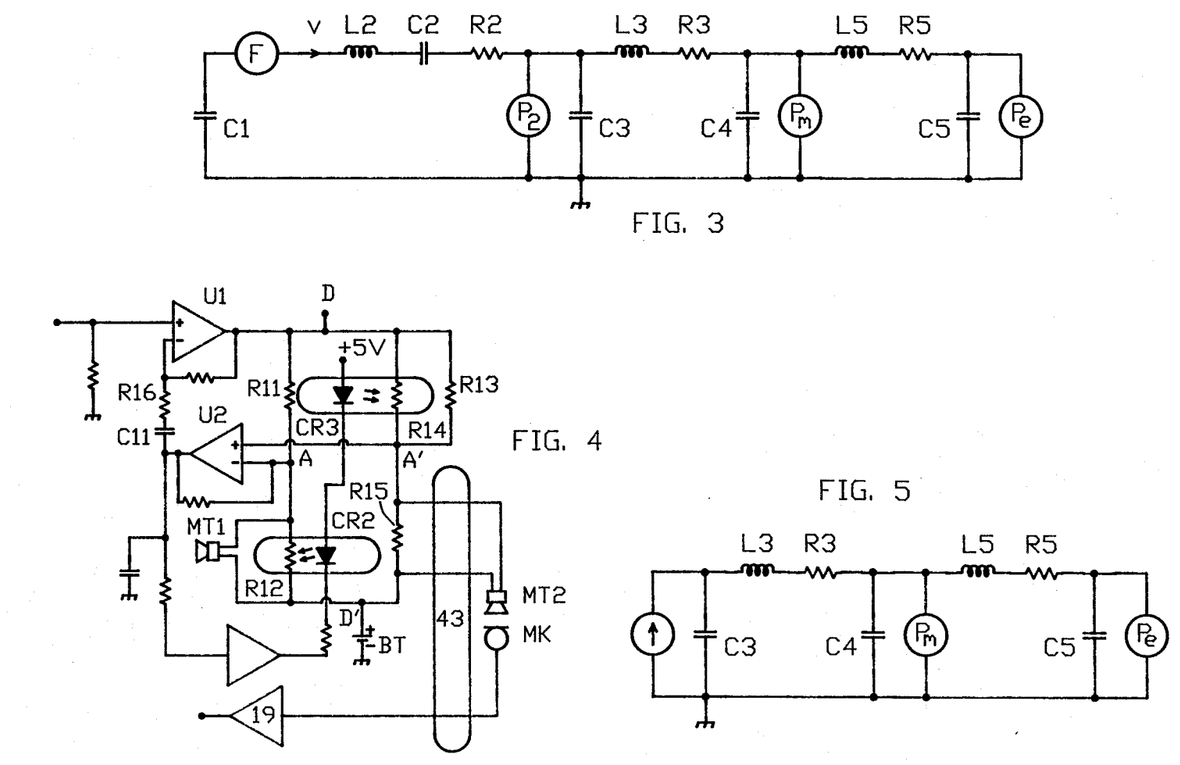
FIG. 3 is an electro-acoustical circuit diagram of the Electronic Earplug (pressure drive).
FIG. 4 is a circuit diagram of the bilateral transducer bridge compensation circuit.
FIG. 5 is an electro-acoustical circuit diagram of the Electronic Earplug driven by a bilateral transducer drive.

Bilateral transducer 21 and summing microphone 31 are electrically connected through a cable 43 to the electronic circuit described in FIG. 5. Electronic Earplug can be self supporting by resting in the concha fossa. Optimally, a bracket not shown connects enclosure 34 to a headband or chin band and provides lateral sealing pressure on earplug adapter 35.

Noise which penetrates to the occluded ear canal 36 travels through opening 33 in flange 38 of earplug adapter 35 and through summing microphone orifice 32, and is sensed by summing microphone 31. The corresponding summing microphone output signal initiates the ANR process.

The Electronic Earplug in FIG. 2 is described in terms of an equivalent acoustical circuit diagram in FIG. 3. Dynamic analogies between electrical, mechanical, and acoustical circuits are well known in the art (e.g. Leo L. Beranek, *Acoustics*, Chapter 3. American Institute of Physics, 1986). It will therefore suffice to say that an impedance analogy is used where force F, or pressure p, correspond to voltage E; velocity v, or mass flow U, corresponds to current i; compliance C corresponds to capacitance C; and mass M corresponds to inductance L.

In FIG. 3, the force F generated by the current i in coil 22 of transducer 21 is:

$$F = Bli \qquad (1)$$

where B is the magnetic flux density and l the length of wire in coil 22.

Force F acts on diaphragm 23 and results in sound pressure $p_1 = F/S$ between the front and back of diaphragm 23, where S is the area of the diaphragm. Diaphragm velocity v is proportional to force F and inversely proportional to mechanical input impedance $Z_a$, which in turn depends on the circuit components in FIG. 3.

Capacitance C1 corresponds to the compliance of the reference chamber 28 in the back of diaphragm 23. Inductance L2, capacitance C2, and resistance R2 correspond to the mass, compliance, and resistance of the diaphragm 23. Capacitance C3 corresponds to the compliance of the forward chamber 29 in front of transducer 21. Acoustical pressure signal in chamber 29 is $p_2$. Inductance L3 and resistance R3 correspond to the acoustical impedance of the coaxial sound passage 30. Capacitance C4 corresponds to the volume of air in front of the summing microphone orifice 32 and pressure $p_m$ represents the sound pressure sensed by the summing microphone 31. Inductance L5 and the resistance R5 corresponds to the impedance of opening 33. Finally C5 corresponds to the compliance of the air volume in the occluded ear canal 36 adjacent to the eardrum 37. Pressure $p_e$ represents the sound pressure acting on the eardrum.

The phase shift of the electro-acoustical transfer function $T_a$ due to acoustic circuit transmission is of critical significance in the design of ANR used with the Electronic Earplug. The stability of the electro-acoustical ANR system depicted in FIG. 1, requires that $|T_a-| < 1$ at a frequency where $T_a$ exhibits a 180° phase shift (e.g., *Feedback and Control Systems*, J. J. DiStefano III et al, McGraw-Hill, 1967).

Typically, the 180° phase shift occurs in 1 kHz to 2.5 kHz region where the magnitude of $T_a$ is close to its peak. Based on stability requirements, these conditions allow little gain margin for noise attenuation when the loop between the summing microphone output and transducer driver input is closed.

In order to improve the response of the acoustical transfer function $T_a$, a bilateral transducer bridge compensation circuit, shown in a schematic diagram in FIG. 4 is used. In FIG. 4, a driver amplifier U1 drives, between point D and bias supply B, a bridge consisting of four arms:

(1) R11,
(2) MT1 in parallel with photoconductive resistor R12,
(3) R13 in parallel with photoconductive resistor R14, and
(4) MT2 in parallel with resistor R15.

Transducer MT2, summing microphone MK, and cable W are equivalent respectively, to the bilateral transducer 21, the summing microphone 31, and the cable 43 in FIG. 2.

Transducers MT1 and MT2 are substantially identical except that MT2 is used to drive the acoustical circuit in the Electronic Earplug, whereas diaphragm of MT1 is blocked and therefore stationary. Transducers MT1 and MT2, within tolerances, are therefore electrically equivalent except that the blocked transducer MT1 does not generate any motion induced voltage.

Bias supply BT creates a dc bias across the bridge. The bias supply presents a short to ground for audio frequencies. Variable resistors R12 and R14 are photoconductors optically coupled to light-emitting diodes CR2 and CR3 respectively, in two opto-coupler units. The higher the current through the photodiode, the more light the photodiode emits causing the variable resistance to decrease.

Variable resistors R12 and R14 are used to provide adaptive bridge balance in spite of such factors as temperature changes, component tolerances, and aging. To explain the operation of adaptive bridge balancing, it will be assumed that the resistance associated with the coil windings of MT2 increases momentarily beyond balance. Such an increase may be caused by an increase in temperature when the Electronic Earplug is first placed in the ear. As a result of such imbalance, the resistance of bridge arm R14-MT2 becomes higher than the resistance of arm R13-R14 causing a drop of bias voltage at A' compared to A. It should be noted that at D there is only an ac signal and zero dc signal.

The AA' potential difference is amplified by bridge sensing amplifier U2. The resulting negative output signal of U2 is separated from the audio signal components by low-pass filters R17 and C12 and is applied to inverting LED driver U3. The resulting output of the U3 driver is more positive and so the current through LED's CR2 and CR3 is lowered. The net result is that the photoconductive resistances R12 and R14 increase until the bridge balance is restored.

Actually, a small constant bridge imbalance is maintained at all times to assure that the common mode ac loop feedback via U1 and U2 is negative and stable. This imbalance is kept small enough so that it can be neglected in the ac bridge analysis which follows.

If an audio signal $E_n$ is applied to the non-inverting input of the driver U1, an amplified audio signal appears at the output of U1 at point D.

If the four arms of the bridge are accurately balanced, the driver voltage at D cancels at the bridge output terminals AA'. However, the voltage induced by the diaphragm velocity of the bilateral transducer MT2 is not balanced out since the coil of transducer MT1 is blocked. Hence, under balanced conditions, the output $E_2$ of the bridge sensing amplifier U2 is proportional to the diaphragm velocity v of MT2:

$$E_2 = G_2 Blu \qquad (2)$$

where $G_2$ is the gain of U2 and B and l have been defined in connection with equation 1.

In essence, the bridge balances out the effect of the drive voltage at D supplied to both bridge branches and retains only the diaphragm velocity-induced signal which is picked up by the bridge sensing amplifier U2 connected to points A and A' on the bridge.

The audio component (from 20 Hz and up) of $E_2$ at the output of U2 is then transmitted through a high-pass filter R16-C11 to the inverting input of the driver amplifier U1 which exhibits a gain G1. The output $E_d$ of the amplifier U1 at the bridge driving point D is therefore:

$$E_d = (E_n - G_2 Blu) G_1 \tag{3}$$

The current through transducer MT2 is $E_d/Z_e$ where $Z_e$ is the series impedance of the third and fourth arm of the bridge. Consequently, as per eq. 1, the force generated by the coil of MT2 is $E_d Bl/Z_e$. Since the force and velocity are by definition related by mechanical impedance $Z_m$, the velocity of the diaphragm is:

$$v = \frac{E_d Bl}{Z_m Z_e} \tag{4}$$

Eliminating the driver output voltage $E_d$ between eqs. 3 and 4 gives the equation for the diaphragm velocity:

$$v = \frac{E_n G_1 Bl}{G_1 G_2 (Bl)^2 + Z_m Z_e} \tag{5}$$

The pertinent aspect of eq. 5 is that if $$G_1 G_2 > \frac{Z_m Z_e}{(Bl)^2} \tag{6}$$

the velocity of the bilateral transducer diaphragm is independent of the acoustical impedance $Z_a$ and is $$v \cong \frac{E_n}{G_2 Bl} \tag{7}$$

Equation 7 indicates that the circuit in FIG. 4 produces diaphragm velocity v proportional to the input signal $E_n$. This in essence means that diaphragm 23 is no longer an acoustical pressure generator but behaves like a constant velocity generator.

The effect of substitution of the constant velocity generator v for F in the acoustical circuit in FIG. 3, is shown in FIG. 5: The pressure $p_2$ in the chamber 29 represented by compliance C3 in front of the bilateral transducer 21, is now independent of C1, L2, C2 and R2 in FIG. 3. This eliminates the effect of the diaphragm resonance on transfer function $T_a$.

The effect on the acoustical transfer function $T_a$ is that the frequency corresponding to the 180° phase shift is moved from 2.5 kHz region towards a higher frequency of typically 6 kHz to 8 kHz which is close to the ultimate delay caused by the velocity of sound. This move significantly improves the operation capability of the active noise cancellation. It also broadens the frequency response and as such can be used to improve fidelity of reproduction in earphone or hearing aid application.

In addition to the high frequency and instability problem associated with $T_a$ when the phase angle of $T_a$ reaches $-180°$, there is also an instability problem in the subaudio region near dc. In that region, $T_a$ exhibits three zeros due to the response of the MT2 transducer, the response of microphone 18, and the response of the bridge. This leads to a $+270°$ phase shift at dc which causes instability when a $+180°$ phase shift is reached in the subaudio region. The solution of low frequency instability is addressed later.

Figure 6:
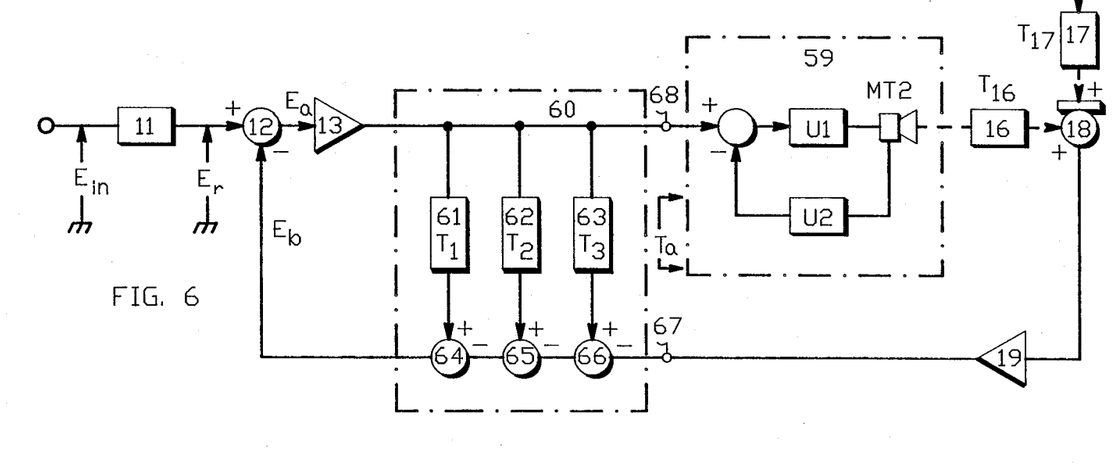
FIG. 6 is a block diagram of an Active Noise Reduction system used with an Electronic Earplug.

A block diagram of the complete ANR system used with the Electronic Earplug is shown in FIG. 6. Transfer function $T_a$ is obtained by ignoring the block diagram elements to the left of points 67 and 68 in FIG. 6 and then measuring the response at point 67 to the unit amplitude frequency sweep at point 68.

The features in FIG. 6 which are common to the state-of-the-art system configuration are designated by the same numbers as in FIG. 1. It can be seen that in addition to the bilateral transducer bridge compensation circuit of FIG. 4 shown abbreviated as block 59, another novel feature is a shunt feedback control network shown as block 60.

Shunt feedback control network 60 consists in general of N filter branches placed in parallel with $T_a$. The shunt feedback control filter branches are connected at one end to the output of the amplifier 13 and at the other end to signal combiners 64, 65, and 66 respectively. In the preferred embodiment shown in FIG. 6, N=3, i.e., there are three parallel filters 61, 62, and 63 characterized by transfer functions $T_1$, $T_2$, and $T_3$ respectively.

The active noise reduction ratio, defined as the ratio of noise at the summing microphone 18 with and without ANR, in the system with a shunt feedback control network in FIG. 6 is:

$$\frac{p_n}{p_{no}} = \frac{1 + A\left(\sum_{i=1}^{N} T_i\right)}{1 + A\left(T_a + \sum_{i=1}^{N} T_i\right)} \tag{8}$$

where A is the gain of the amplifier 13. Without shunt feedback control compensation (N=0), the maximum gain A is limited by the high and low stability conditions of $T_a$ discussed earlier.

In the preferred embodiment N=3 and so $$\frac{p_n}{p_{no}} = \frac{1 + A(T_1 + T_2 + T_3)}{1 + A(T_a + T_1 + T_2 + T_3)} \tag{9}$$

Filter 63 is used for high frequency stabilization of the ANR system. Transfer function $T_3$ of filter 63 is such that $|T_3| << |T_a|$ at lower audio frequencies up to a few kilohertz. In the higher frequency range, typically 6-10 kHz, where $T_a$ goes through a $-180°$ phase transition, $T_3$ increases so that $|T_3| > |T_a|$. Therefore, above approximately 5 kHz, the stability of the loop no longer depends on $T_a$ but it is in fact dominated by $T_3$.

Such a $T_3$ response can be obtained by implementing $T_3$ in a number of ways, i.e., as a high pass, a bandpass, a high-pass notch filter, or their combination. The preferred embodiment uses a band pass filter described by Eq. 10:

$$T_3 = \frac{k_3 \omega_3 s / Q_3}{s^2 + \omega_3 s / Q_3 + \omega_3^2} \tag{10}$$

where s is complex frequency in Laplace transformation, $k_3=2.5$ is a gain factor, $\omega_3=4.9$ kHz is the center frequency and $Q_3=1.3$ is the Q factor of the bandbass filter.

Filter 61 is used for low frequency stabilization of the ANR system. The transfer function of filter 61 is T1. Generally $|T_1|<<|T_a|$ throughout the audio frequency spectrum. However in the sub-audio region, near dc, where the angle of $T_a$ approaches $+180°$, $T_1$ increases so that $|T_1|>|T_a|$. Transfer function $T_1$ therefore dominates the stability conditions near dc. The preferred embodiment uses a low-pass filter with gain which is characterized by Eq. 11:

$$T_1 = \frac{k_1\omega_1 s}{s + \omega_1} \quad (11)$$

where $k_1=4$ is a gain factor, and $\omega_1=1$ Hz is the 3 decibel cutoff frequency of the low-pass filter.

Branch 62 is used to null the noise at a specific cancellation frequency. A look at the numerator of eq. 9 shows that one can reduce noise to zero if $$1+A(T_1+T_2+T_3)=0 \quad (12)$$

so that the response of $T_2$ of filter 62 is $$T_2 = -(1/A+T_1+T_3) \quad (13)$$

The response $T_2$ is typically implemented as a bandpass filter such that at the center frequency $f_o$ is well above the 3 decibels point of $T_1$ and well below the 3 decibels point of $T_3$.

It should be noted that $T_2$ is negative, which means that on its own, it creates positive feedback instability. However, cancellation frequency $f_o$ is typically in middle range of ANR operation where $T_2<<T_a$. The stability of the system is therefore dominated by $T_a$. In the preferred embodiment, $T_3$ is implemented by a series combination of bandpass and low-pass filters described by:

$$T_2 = \frac{k_2\omega_{21}s^2/Q_2}{(s^2 + 2\omega_{21}/Q_2 + \omega_{21}^2)\cdot(s+\omega_{22})} \quad (14)$$

where $k_2=0.25$ is a gain factor, $\omega_{21}=3.1$ kHz is the center frequency of the bandpass element, $Q_2=1$ is the Q factor of the bandpass element, and $\omega_n=3.1$ kHz is the 3 decibel cutoff frequency of the high-pass element. Gain A of amplifier 13 is 100.

Analog circuits which implement filters of the preferred embodiment defined in eqs. 10, 11, and 14 are well known (e.g., *Analog Filter Design*, M. E. Van Valkenburg, Holt Rinehart & Winston, 1982). Switched capacitor implementation of the above filter is also straight forward. Shunt feedback control network implementation lends itself well to the known art of digital filters (e.g., Antoniou, A. *Digital Filters: Analysis and Design*, McGraw-Hill, 1979). A digital filter implementation of shunt feedback control network 60 has no physical branches 61, 62, and 63. In its place, the digital filter is designed by one of several analog-to-digital mapping techniques which map responses $T_1$, $T_2$, and $T_3$ into a digital filter algorithm. Even though the physical form of an analog filter and a digital signal processor is very different, the function of both filters is to perform high and low-frequency stabilization and noise nulling. It should be pointed out that clock feedthrough in the shunt feedback control filter is mocked in the active ANR region by inherently analog electro-acoustical transfer function $T_a$.

Hybrid implementation in which shunt feedback control filters are analog but their parameters, such as gain Q or $W_o$ are digitally controlled is advantageous in some situations.

Analog implementation of a large number of branches is cumbersome. Digital implementation on the other hand lends itself to simulation of many filters. Also, digital filter implementation of the shunt feedback control function can address more readily the minimization of noise enhancement in the crossover region. Specifically, digital filters allow a design which assures the $p_n/p_{no}$ in less than a prescribed minimum in the operational range and that the noise enhancement is no more than a prescribed maximum elsewhere.

The communication input signal $E_{in}$ in FIG. 6 is applied to the pre-emphasized filter in the block 11. This pre-processing compensates for the change of the response of the circuit caused by ANR. This change is $$\frac{p}{E_r} = \frac{1}{1 + A\left(T_a + \sum_{i=1}^{N} T_i\right)} \quad (15)$$

The origin of the communication input signal $E_{in}$ depends on application. Applications are divided here into four categories: carrier communication, wire communication, local communication, and open loop compensation.

In carrier communication systems, the original acoustical signal modulates a carrier such as FM or AM radio, infrared or ultrasonic wave. This carrier is locally detected and converted to $E_{in}$. An example of such application is aircraft communication where bulky headphones can be replaced by an Electronic Earplug system based on system in FIG. 6.

An example of wire communication application is a replacement of telephone receiver by the system in FIG. 6 which provides much improved operation in noisy location.

In local communication application, signal $E_{in}$ originates from amplified and processed signal picked up by local external microphone. One example of such application is a hearing aid with a directional external microphone. Such a directional external microphone picks up preferentially speech from one source while the ANR feature reduces unwanted ambient sounds.

Another application of local communication application is hearing protection for impulse noise. In this application, the reference chamber 28 in FIG. 2 is open to ambient air, either directly, or through a non-linear sonic valve which transmits better at low than at high sound pressure levels. Amplifier 13 in FIG. 6 has now a non-linear and approximately exponential response characteristics, so that it produces little output at low signal levels, but has an increasing gain with higher input. For low signal levels, such a non-linear ANR system allows normal hearing with no electronic modification. However, at high signal levels, the noise reduction feature is activated thus protecting the hearing from noise impulse.

Yet another local communication application is a stethoscope where the ANR feature helps in patient examination in noisy wards.

Signal $E_{in}$ obtained from local external microphone can also be used for open loop improvement of noise reduction. In this application, a local external microphone samples external noise $p_n$. Block 11 in FIG. 6 in this application is an adaptive filter with a transfer function similar to $T_{17}$, but of opposite phase, so that signal $E_{in}$ reduces noise at the microphone 18. Such an open loop method of noise reduction is well known as adaptive noise canceling (see e.g., B. Widrow et al, *Proc. IEEE* Vol. 63, No. 12, pp 1697-1716. December, 1975). The above combined system of open and feedback noise reduction has advantages as compared with either of the two methods alone. For example, combined feedback/open loop system can compensate for vibrational microphone pickup of external noise $p_n$ which otherwise provides the lower limit on the noise reduction of a feedback system. The combined feedback/open loop system has much less stringent requirement of the adaptability and speed of the open loop filter and so leads to a less costly and bulky system.

Figure 7:
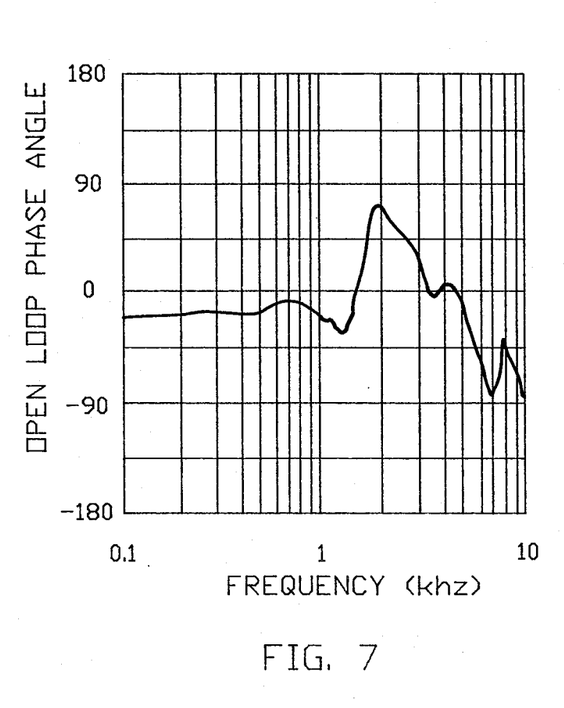
FIG. 7 shows a phase component of an open loop gain of the Active Noise Reduction system in FIG. 6 including effects of a shunt feedback control circuit.
Figure 8:
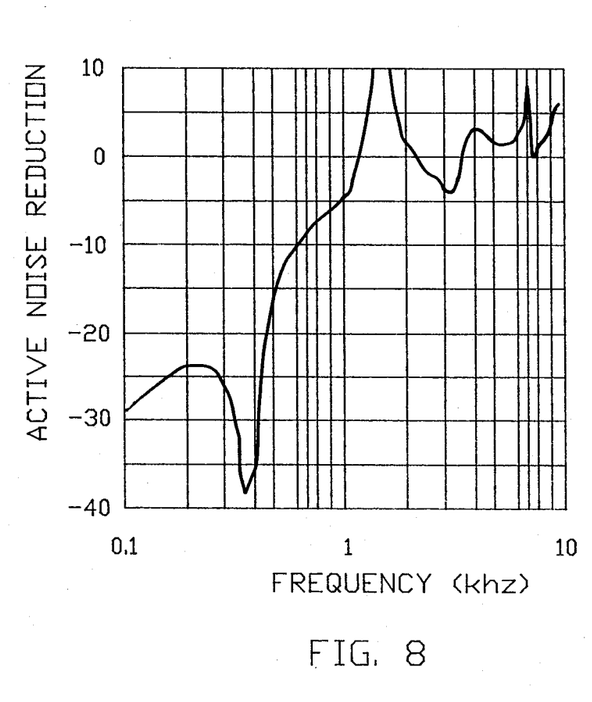
FIG. 8 shows the noise attenuation of the Active Noise Reduction system in FIG. 6 including effects of a shunt feedback control circuit.

Typical results which are accomplished by a linear ANR circuit without open loop compensation in FIG. 6, using the three analog filters 61, 62, and 63, are shown in FIGS. 7 and 8. FIG. 7 shows the phase component of the ANR loop gain. It can be seen that the shunt feedback control stabilization has removed the 180° phase shift. It can be seen in FIG. 8 that ANR system of this invention is very effective in increasing the noise attenuation of the earplug in the lower audio-frequency range where passive earplugs are not effective. At a higher audio-frequency range (above 1 kHz), passive earplug attenuation is usually quite adequate. Consequently the Electronic Earplug accomplishes excellent noise attenuation in the entire acoustical frequency region.

While certain specific embodiments of improved Active Noise Reduction System and devices have been disclosed in the foregoing description, it will be understood that various modifications within the scope of the invention may occur to those skilled in the art. Therefore, it is intended that adaptations and modifications should and are intended to be comprehended within the meaning and range of equivalents of the disclosed embodiments.

What is claimed is:

1. An earplug for placement in an ear canal with communication capability provided by a speaker, comprising:
   a speaker for converting an electrical signal into an acoustical output;
   a summing microphone;
   an external active noise reduction circuit;
   a cable connecting the speaker and the summing microphone to said external active noise reduction circuit;
   an enclosure for supporting said speaker, said summing microphone, and said cable;
   a hollow earplug adapter, the enclosure being mounted inside of said hollow earplug adapter, the enclosure and said earplug adapter having openings allowing close acoustical coupling among the speaker, the summing microphone, and the ear canal; and
   said hollow earplug adapter forming an acoustical seal between the enclosure, a concha fossa and/or an ear canal wall, thereby acoustically isolating a small volume of the ear canal from ambient noise providing a quiet zone for active noise reduction.

2. An earplug in accordance with claim 1, wherein said enclosure and said hollow earplug adapter are shaped to nest for support inside said concha fossa.

3. An earplug in accordance with claim 1, wherein said hollow earplug adapter comprises a pliable elastomer skin covering a portion of said enclosure and a plastic foam backing.

4. An earplug in accordance with claim 1, further comprising:
   a non-linear acoustical element between said ear canal and ambient air, said element attenuating noise at high sound pressure levels more than at low sound pressure levels; and
   said active noise reduction circuit also having a non-linear response
so as to allow direct aural communication at low sound levels while actively attenuating ambient noise amplitude above a prescribed level.

5. An earplug in accordance with claim 1, wherein the active noise reduction circuit further comprises:
   an electronic stethoscope type of
   microphone for detection of cardiovascular sounds and respiratory sounds, connected to a preamplifier/filter circuit which processes an output signal of said stethoscope type of microphone to produce an input to the active noise reduction circuit.

6. An earplug in accordance with claim 1, wherein the active noise reduction circuit further comprises:
   a hearing aid type of
   microphone for detection of speech and sounds; and
   a preamplifier/filter circuit which processes an output signal of said hearing-aid type of microphone to produce an input to the active noise reduction circuit.

7. A bridge circuit comprising
   four arms, each arm joined to its neighbor at four terminals, a first terminal and a third terminal forming driving terminals, and a second terminal and a fourth terminal forming sensing terminals of said bridge circuit;
   a first arm of said four arms comprising a speaker coil;
   a second arm, a third arm, and a fourth arm of said four arms formed by impedances selected for obtaining a nominal balance of the bridge circuit;
   means for applying an ac driving voltage and a dc bias to said driving terminals;
   means for decoupling a dc signal resulting from said dc bias and indicating a bridge unbalance, and an ac signal at the sensing terminals;
   means for modifying at least one impedance of at least one of said four arms in response to the dc signal at said sensing terminals for adaptively improving said balance of the bridge circuit when the at least one impedance of the bridge arms, including speaker coil, change.

8. In an active noise reduction system of an electro-acoustical negative feedback type wherein an amplifier amplifies an actuating signal, the amplified actuating signal is applied to a speaker for converting the amplified actuating signal to an acoustical signal, a sum of the acoustical signal and ambient noise is picked up by a summing microphone and amplified by a preamplifier, wherein further a signal combiner subtracts a primary feedback signal provided by an output of the summing microphone from a reference signal to generate the actuating signal, thereby closing an electro-acoustical negative feedback loop, a combination with said speaker means comprising a secondary feedback loop, further comprising:
- a bilateral transducer means having driving terminals, sensing terminals, and a diaphragm;
- a driver amplifier, having an input and an output, the output of said driver amplifier connected to the driving terminals for driving the diaphragm in a speaker mode; and
- a sensing amplifier connected to the sensing terminals of the bilateral transducer means for sensing a motion of said diaphragm in a microphone mode, an output of said sensing amplifier combined with a secondary feedback loop input signal to form a signal applied to the driver amplifier input, thereby closing the secondary feedback loop.

9. An active noise reduction system of an electroacoustical negative feedback type, wherein an amplifier amplifies an actuating signal, the amplified actuating signal is applied to a speaker for converting the amplified actuating signal to an acoustical signal, a sum of the acoustical signal and ambient noise is picked up by a summing microphone and amplified by a preamplifier, wherein further a signal combiner subtracts a primary feedback signal, provided by an output signal of the summing microphone from a reference signal to generate the actuating signal, thereby closing an electroacoustical negative feedback loop, comprising:
- an enclosure for providing passive attenuation, for acoustically isolating a quiet zone from ambient noise, said enclosure mechanically supporting said speaker and said summing microphone, and for keeping said speaker and said summing microphone acoustically coupled within the quiet zone; and
- a shunt feedback control network means with at least one input node and at least one output node, said at least one input node and said at least one output node connected between two nodes of the electroacoustical negative feedback loop to form a shunting auxiliary loop for enhancing and stabilizing negative feedback, thereby influencing system stability and modifying a level of ambient noise in the quiet zone.

10. A system in accordance with claim 13, wherein the shunt control network comprises a switched capacitor filter.

11. A system in accordance with claim 13, wherein the shunt control network comprises a digital signal processor.

12. A system in accordance with claim 9, comprising:
- an external microphone for sensing ambient noise; and
- a filter used as a noise filter for processing an output of said external microphone, an output of said noise filter combined in the signal combiner with the primary feedback signal to form the actuating signal for reducing an effect of the ambient noise in the quiet zone.

13. A system in accordance with claim 9, wherein the shunt feedback control network means comprises at least one filter, an input of the at least one filter derived from the actuating signal, an output of the at least one filter combined with said output signal of the summing microphone, and applied to the signal combiner.

14. A system in accordance with claim 9, comprising a filter used as a pre-emphasis filter having an input and an output, with a communication input signal applied to the input of the pre-emphasis filter and the reference signal produced at the output of the pre-emphasis filter, a frequency response of the pre-emphasis filter modifying the reference signal for sound at the summing microphone to be more closely proportional to the communication input signal.

15. A system in accordance with claim 9, comprising a secondary feedback loop, further comprising:
- a bilateral transducer means having driving terminals, sensing terminals, and a diaphragm;
- a driver amplifier, having an input and an output, the output of said driver amplifier connected to the driving terminals for driving the diaphragm in a speaker mode; and
- a sensing amplifier connected to the sensing terminals of the bilateral transducer means for sensing a motion of said diaphragm in a microphone mode, an output of said sensing amplifier combined with a secondary feedback loop input signal to form a signal applied to the driver amplifier input, thereby closing the secondary feedback loop.

16. A system in accordance with claim 15, further comprising:
- means for applying a dc bias to the driving terminals;
- means for decoupling a dc signal and an ac signal at the sensing terminals; and
- means for adaptively improving performance of the secondary feedback loop by adaptively modifying its response based on the dc signal at the sensing terminals.

17. A system in accordance with claim 9, wherein
said enclosure supports said speaker and said microphone in proximity of an ear canal, said enclosure acoustically sealing said quiet zone around the ear canal.

18. An earplug in accordance with claim 1, wherein said earplug adapter can be readily removed from said enclosure and replaced onto said enclosure.

* * * * *